United States Patent [19]

Sirrenberg et al.

[11] 4,276,310
[45] Jun. 30, 1981

[54] COMBATING PESTS WITH N-(4-SUBSTITUTED-PHENYL)-N'-(2-SUBSTITUTED-BENZOYL)-THIOUREAS

[75] Inventors: Wilhelm Sirrenberg, Sprockhoevel; Erich Klauke, Odenthal; Ingeborg Hammann, Cologne; Ingomar Krehan, Cologne; Peter Kraus, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 67,246

[22] Filed: Aug. 16, 1979

[30] Foreign Application Priority Data

Aug. 24, 1978 [DE] Fed. Rep. of Germany ....... 2837086

[51] Int. Cl.$^3$ .................... C07C 157/12; A01N 47/30
[52] U.S. Cl. ...................................... 424/322; 564/23; 564/44
[58] Field of Search ...................... 260/552 R, 553 E; 424/322

[56] References Cited

U.S. PATENT DOCUMENTS

| | | | |
|---|---|---|---|
| 3,406,192 | 10/1968 | Speziale et al. | 260/553 E X |
| 4,013,717 | 3/1977 | Wellings et al. | 260/553 E |
| 4,085,226 | 4/1978 | Sirrenberg et al. | 260/553 E X |
| 4,089,975 | 5/1978 | Wade et al. | 260/553 E X |
| 4,160,037 | 7/1979 | Kaugars | 424/322 |
| 4,162,330 | 7/1979 | Ehrenfreund | 260/553 E X |
| 4,170,657 | 10/1979 | Rigterink | 260/553 E X |

FOREIGN PATENT DOCUMENTS

45-15518 5/1970 Japan ................................ 260/552 R

OTHER PUBLICATIONS

Oliver et al., J. Agr. Food Chem., vol. 24, No. 5, 1976, pp. 1065–1068.

Primary Examiner—Thomas A. Waltz
Attorney, Agent, or Firm—Sprung, Felfe, Horn, Lynch & Kramer

[57] ABSTRACT

N-(4-Substituted-phenyl)-N'-(2-substituted-benzoyl)-thioureas of the formula

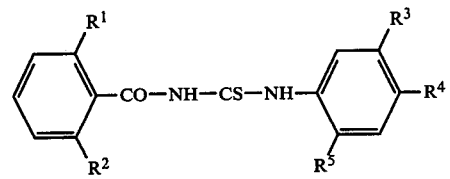

in which
$R^1$ represents halogen,
$R^2$ represents hydrogen or halogen,
$R^3$ represents hydrogen, halogen or halogenoalkyl,
$R^4$ represents halogen, halogenoalkyl, halogenoalkoxy, halogenoalkylthio or halogenoalkylsulphonyl, with the proviso that $R^3$ represents halogenoalkyl if $R^4$ represents halogen, and
$R^5$ represents hydrogen or halogen, which possess arthropodicidal, fungicidal and bactericidal properties.

11 Claims, No Drawings

COMBATING PESTS WITH N-(4-SUBSTITUTED-PHENYL)-N'-(2-SUBSTITUTED-BENZOYL)-THIOUREAS

The present invention relates to and has for its objects the provision of particular new N-(4-substituted-phenyl)-N'-(2-substituted-benzoyl-thioureas which possess pesticidal properties, active compositions in the form of mixtures of such compounds with solid and liquid dispersible carrier vehicles, and methods for producing such compounds and for using such compounds in a new way especially for combating pests, e.g. insects, acarids, fungi and bacteria, with other and further objects becoming apparent from a study of the within specification and accompanying examples.

It has already been disclosed that certain substituted benzoyl-thioureas, for example N-(2,6-dichlorobenzoyl)-N'-(3,4-dichlorophenyl)-thiourea, have an insecticidal action (see U.S. Pat. No. 3,933,908).

It is also known that certain copper compounds, for example copper oxychloride, have fungicidal and bactericidal properties.

The present invention now provides, as new compounds, the N-phenyl-N'-benzoyl-thioureas of the general formula

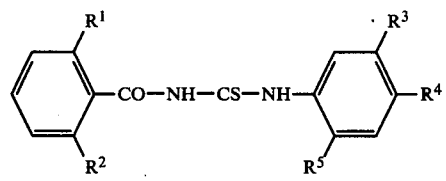

in which
R$^1$ represents halogen,
R$^2$ represents hydrogen or halogen,
R$^3$ represents hydrogen, halogen or halogenoalkyl,
R$^4$ represents halogen, halogenoalkyl, halogenoalkoxy, halogenoalkylthio or halogenoalkylsulphonyl, with the proviso that R$^3$ represents halogenoalkyl if R$^4$ represents halogen, and
R$^5$ represents hydrogen or halogen.

Preferably, in formula (I), R$^1$ represents fluorine, chlorine, bromine or iodine, R$^2$ represents hydrogen, fluorine, chlorine, bromine or iodine, R$^3$ represents hydrogen, chlorine or trifluoromethyl, R$^4$ represents chlorine, fluoro- or chlorofluoroalkyl, fluoro- or chlorofluoro-alkoxy, fluoro- or chlorofluoro-alkylthio or fluoroalkylsulphonyl, the halogenoalkyl group in each case containing 1 or 2 carbon atoms, with the proviso that R$^3$ represents trifluoromethyl if R$^4$ represents chlorine, and R$^5$ represents hydrogen or chlorine.

Surprisingly, the N-phenyl-N'-benzoyl-thioureas according to the invention exhibit a considerably better activity as agents for combating pests, in particular a considerably higher insecticidal action, than the very closely related known benzoyl-thioureas, and a considerably better bactericidal action than copper oxychloride, which is known. They are also fungicidally active. The products according to the present invention thus represent a valuable enrichment of the art.

The invention also provides a process for the preparation of an N-phenyl-N'-benzoyl-thiourea of the formula (I), in which a benzoyl isothiocyanate of the general formula

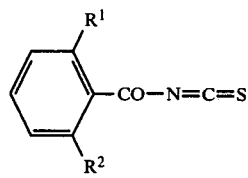

in which R$^1$ and R$^2$ have the meanings stated above, is reacted with a substituted aniline of the general formula

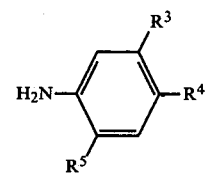

in which R$^3$, R$^4$ and R$^5$ have the meanings stated above, if appropriate using an inert diluent.

If, for example, 2,6-dichlorobenzoyl isothiocyanate and 4-trifluoromethoxy-aniline are used as starting materials, the reaction of these compounds can be outlined by the equation which follows:

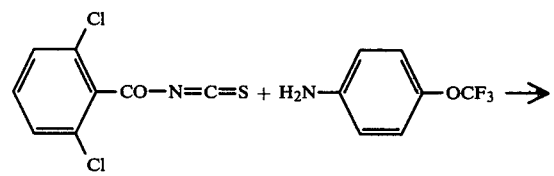

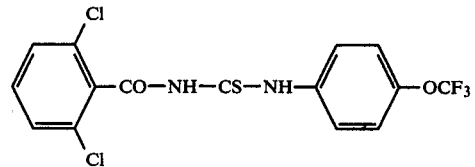

The formulae (II) and (III) provide general definitions of the starting materials to be used.

Benzoyl isothiocyanates of the formula (II) to be used as starting compounds are known, and they can be prepared by processes which are known from the literature (see Houben-Weyl, Methoden der organischen Chemie (Methods of Organic Chemistry), 4th edition, Volume 9, pages 878–879, Georg Thieme Verlag, Stuttgart 1955). They are obtained, in particular, in high purity by reacting trimethylsilanyl isothiocyanate with the corresponding substituted benzoyl halides at temperatures between 100° and 250° C. (see DE-AS (German Published Specification) 1,215,144).

Examples which may be mentioned of the benzoyl isothiocyanates of the formula (II) are: 2-fluoro-, 2-chloro-, 2-bromo- and 2-iodo-benzoyl isothiocyanate, 2,6-difluoro- and 2,6-dichloro-benzoyl isothiocyanate and 2-chloro-6-fluoro-benzoyl isothiocyanate.

Substituted anilines of the formula (III) also to be used as starting substances are likewise known, and they can be prepared by known processes (see, for example, J.Org.Chem. 29 (1964), 1-11 and U.S. Pat. No. 3,387,037).

Examples which may be mentioned of the substituted anilines of the formula (III) are: 4-trifluoromethyl-aniline, 3,4-bis-trifluoromethyl-aniline, 2-chloro-4-trifluoromethyl-aniline, 3-chloro-4-trifluoromethyl-aniline, 4-chloro-3-trifluoromethyl-aniline, 4-difluoromethoxyaniline, 4-trifluoromethoxy- and 4-trifluoromethylthio-aniline, 2-chloro- and 3-chloro-4-trifluoromethoxyaniline, 2-chloro- and 3-chloro-4-trifluoromethylthio-aniline, 4-chlorodifluoromethoxy- and 4-chlorodifluoromethylthio-aniline,. 2-chloro- and 3-chloro-4-chlorodifluoromethoxy-aniline, 2-chloro- and 3-chloro-4-chlorodifluoromethylthio-aniline, 4-(2-chloro-1,1,2-trifluoroethoxy)- and 4-(2-chloro-1,2,2-trifluoroethylthio)-aniline, 2-chloro- and 3-chloro-4-(2-chloro-1,1,2-trifluoroethoxy)-aniline, 2-chloro- and 3-chloro-4-(2-chloro-1,1,2-trifluoro-ethylthio)-aniline, 4-trifluoromethylsulphonyl-aniline and 2-chloro- and 3-chloro-4-trifluoromethylsulphonyl-aniline.

The process for the preparation of the N-phenyl-N'-benzoyl-thioureas according to the invention is preferably carried out using a suitable solvent or diluent. Possible solvents or diluents are virtually any of the inert organic solvents, especially aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

The reaction temperature can be varied within a substantial range. In general, the reaction is carried out at from 0° to 150° C., preferably at from 20° to 100° C. In general, the process according to the invention is carried out under normal pressure.

The starting materials are usually employed in equimolar amounts for carrying out the process according to the invention. An excess of one or the other of the reactants brings no considerable advantages. The reaction is in general carried out in a suitable diluent and the reaction mixture is stirred for one or more hours at the required temperature. Thereafter, the reaction mixture is allowed to cool to room temperature and the product which has crystallized out is filtered off. The melting point is used for the characterization.

The N-phenyl-N'-benzoyl-thioureas according to the invention are distinguished by an outstanding insecticidal activity. Furthermore, they exhibit a very good activity against phytopathogenic bacteria and fungal diseases.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix,* Pemphigus spp., *Pediculus humanus corporis, Haematopinus* spp. and *Linognathus* spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp.,

*Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., *Ornithodoros spp., Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal, fungicidal or bactericidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or phytopathogenic fungi or bacteria which comprises applying to the arthropods, fungi or bacteria, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods, fungi or bacteria by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

The preparation of the novel compounds is shown in the following illustrative examples:

EXAMPLE 1

(a) The benzoyl isothiocyanates of the general formula

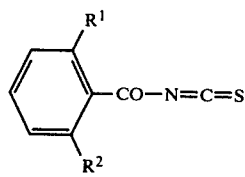
(II)

used as starting compounds and listed below were prepared analogously to Example 1 of DE-AS No. (German Published Specification) 1,215,144:

TABLE 1

| Starting Material (II) | $R^1$ | $R^2$ | Boiling point (°C. at 2 m bars) | Refractive index | Yield (% of theory) |
|---|---|---|---|---|---|
| a | F | H | 104 | $n_D^{20}$:1.6200 | 79 |
| b | Br | H | 140 | $n_D^{20}$:1.6702 | 85.5 |
| c | I | H | 148 | | 76.5 |
| d | Cl | H | 106 | $n_D^{20}$:1.6495 | 87.5 |
| e | Cl | F | 104 | $n_D^{20}$:1.6018 | 93 |
| f | Cl | Cl | 114 | $n_D^{20}$:1.6205 | 77 |
| g | F | F | 98 | $n_D^{20}$:1.5872 | 88 |

(b) 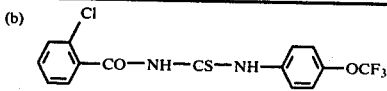
(1)

6 g of 2-chloro-benzoyl isothiocyanate (boiling point 105°–106° C./2 mm Hg; $n_D^{20}$=1.6495) in 20 ml of toluene were added dropwise to a solution of 5.4 g (0.03 mol) of 4-trifluoromethoxy-aniline in 50 ml of toluene at 60° C. The mixture was stirred at 80° C. for one hour. After cooling the mixture to room temperature, the crystalline product was filtered off. It had a melting point of 197° C. It was identified by elementary analysis and NMR spectroscopy. The yield was 6.1 g (54% of theory) of N-(2-chlorobenzoyl)-N'-(4-trifluoromethoxy-phenyl)-thiourea.

EXAMPLE 2

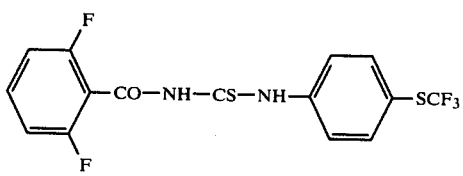
(2)

A solution of 6 g of 2,6-difluorobenzoyl isothiocyanate (boiling point 98° C./1 mm Hg, $n_D^{20}$:1.5872) in 20 ml of toluene was added to a solution of 5.8 g (0.03 mol) of 4-trifluoromethylmercaptoaniline in 60 ml of toluene and the mixture was stirred at 80° C. for one hour. On cooling, the product precipitated. It was filtered off and washed with petroleum ether. The substance melted at 207° C. It was identified by elementary analysis and NMR spectroscopy.

Yield: 9.6 g (81.5% of theory) of N-(2,6-difluorobenzoyl)-N'-(4-trifluoromethylthio-phenyl)-thiourea.

The following compounds of the general formula

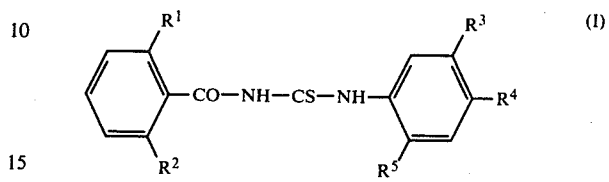
(I)

were obtained analogously:

TABLE 2

| Compound | $R^1$ | $R^2$ | $R^3$ | $R^4$ | $R^5$ | Melting point (°C.) | Yield (% of theory) |
|---|---|---|---|---|---|---|---|
| 3 | Br | H | H | $OCF_2Cl$ | H | 163 | 84.5 |
| 4 | Cl | H | H | $CF_3$ | H | 197 | 74 |
| 5 | Cl | H | H | $OCF_2Cl$ | H | 157 | 36 |
| 6 | Cl | H | Cl | $SCF_3$ | H | 128 | 45.5 |
| 7 | Cl | H | Cl | $OCF_2$—CHFCl | H | 160 | 79.5 |
| 8 | Cl | H | Cl | $OCF_3$ | H | 158 | 72.5 |
| 9 | Cl | H | H | $OCF_2$—CHFCl | H | 160 | 72 |
| 10 | Cl | H | Cl | $SCF_2Cl$ | H | 118 | 55 |
| 11 | Cl | H | Cl | $CF_3$ | H | 173 | 74.5 |
| 12 | Br | H | H | $OCF_3$ | H | 176 | 71.5 |
| 13 | Br | H | H | $SCF_3$ | H | 158 | 50 |
| 14 | Br | H | H | $CF_3$ | H | 200 | 80 |
| 15 | Br | H | $CF_3$ | $CF_3$ | H | 163 | 95.5 |
| 16 | Br | H | Cl | $CF_3$ | H | 187 | 64.5 |
| 17 | Br | H | H | $CF_3$ | Cl | 149 | 89.5 |
| 18 | Br | H | Cl | $OCF_2$—CHFCl | H | 164 | 90 |
| 19 | Br | H | Cl | $SCF_2Cl$ | H | 126 | 84 |
| 20 | Br | H | H | $OCF_2$—CHFCl | H | 170 | 95.5 |
| 21 | Br | H | H | $SO_2CF_3$ | H | 165 | 91 |
| 22 | Br | H | Cl | $OCF_3$ | H | 168 | 97 |
| 23 | Br | H | Cl | $SCF_3$ | H | 138 | 88.5 |
| 24 | Cl | H | $CF_3$ | $CF_3$ | H | 148 | 80.5 |
| 25 | Br | H | H | $OCF_2CHFCl$ | Cl | 158 | 84.5 |
| 26 | I | H | H | $SCF_3$ | H | 174.5 | 76 |
| 27 | F | H | H | $CF_3$ | H | 116–120 | 85.5 |
| 28 | F | H | Cl | $OCF_2$—CHFCl | H | 98–100 | 62 |
| 29 | Cl | H | $CF_3$ | Cl | H | 180 | 81 |
| 30 | Cl | Cl | H | $OCF_3$ | H | 215.5 | 66 |
| 31 | Cl | Cl | Cl | $OCF_2$—CHFCl | H | 207.5 | 71.5 |
| 32 | Cl | Cl | H | $SO_2CF_3$ | H | 232 | 77.5 |
| 33 | Cl | Cl | H | $OCF_2$—CHFCl | H | 210 | 69 |
| 34 | Cl | Cl | Cl | $SCF_2Cl$ | H | 188 | 62.5 |
| 35 | Cl | Cl | Cl | $OCF_3$ | H | 221 | 76 |
| 36 | Cl | Cl | H | $OCF_2Cl$ | H | 201 | 77.5 |
| 37 | Cl | F | H | $OCF_3$ | H | 187 | 76.5 |
| 38 | Cl | F | H | $CF_3$ | H | 226 | 78 |
| 39 | Cl | F | H | $SCF_3$ | H | 180 | 57 |
| 40 | Cl | F | Cl | $OCF_3$ | H | 198 | 91 |
| 41 | Cl | F | H | $OCF_2$—CHFCl | H | 195 | 90 |
| 42 | Cl | F | Cl | $SCF_2Cl$ | H | 163 | 76.5 |
| 43 | Cl | F | H | $SO_2CF_3$ | H | 208 | 88 |
| 44 | Cl | F | H | $CF_3$ | Cl | 202 | 90 |
| 45 | Cl | F | Cl | $OCF_2$—CHFCl | H | 158 | 95.5 |
| 46 | Cl | F | H | $OCF_2Cl$ | H | 175 | 94.5 |
| 47 | Cl | F | $CF_3$ | $CF_3$ | H | 215 | 89 |
| 48 | Cl | F | $CF_3$ | Cl | H | 230 | 94.5 |
| 49 | Cl | F | H | $OCF_2CHFCl$ | Cl | 182 | 85 |
| 50 | Cl | F | Cl | $SCF_3$ | H | 177 | 94.5 |
| 51 | Cl | F | Cl | $CF_3$ | H | 215 | 86.5 |
| 52 | F | F | H | $CF_3$ | H | 210 | 90.5 |
| 53 | F | F | H | $OCF_3$ | H | 180 | 97.5 |
| 54 | Cl | F | H | $OCHF_2$ | H | 179 | 95.0 |
| 55 | F | F | Cl | $SCF_2Cl$ | H | 151 | 82.0 |
| 56 | F | F | H | $OCF_2CHFCl$ | H | 182 | 89.0 |
| 57 | F | F | $CF_3$ | $CF_3$ | H | 186 | 92.5 |
| 58 | F | F | H | $OCHF_2$ | H | 174 | 93.5 |

The pesticidal activity of the compounds of this invention is illustrated by the following examples wherein the compounds according to the present invention are each identified by the number (given in brackets) from preparative Examples 1 and 2 hereinabove.

EXAMPLE 3

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of active compound of the desired concentration and were infested with caterpillars of the diamond-back moth (*Plutella maculipennis*), as long as the leaves were still moist.

After the specified period of time, the destruction was determined.

In this test, for example, the following compounds showed a superior activity compared with the prior art: (11), (51), (16), (6), (39), (50), (2), (13), (23), (8), (30), (40), (22), (5), (46), (3), (9), (7), (28), (18), (10) and (21).

EXAMPLE 4

Laphygma test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified period of time, the destruction was determined.

In this test, for example, the following compounds showed a superior activity compared with the prior art: (4), (38), (52), (1), (53), (43), (54) and (41).

EXAMPLE 5

Mosquito larvae test

Test insects: *Aedes aegypti* larvae, 2nd stage
Solvent: 99 parts by weight of acetone
Emulsifier: 1 part by weight of benzylhydroxydiphenyl polyglycol ether To produce a suitable preparation, the active compound was dissolved, at a rate of 2 g per liter, in the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined.

In this test, for example, the following compounds showed a superior action compared with the prior art: (30), (4), (1), (6), (7), (5), (36), (37), (53), (13), (8), (24), (9), (10), (29), (11), (44), (45), (19), (20), (22), (3), (16), (23) and (25).

EXAMPLE 6

Test with parasitic fly larvae

Emulsifier: 80 parts by weight of alkylaryl polyglycol ether

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction was determined.

In this test, for example, the following compounds showed a superior action compared with the prior art: (37), (53), (8), (11), (41), (42), (40), (19), (39), (52), (2) and (46).

EXAMPLE 7

Bacteria test/*Xanthomonas oryzae*

Solvent: 11.75 parts by weight of acetone
Dispersing agent: 0.75 part by weight of alkylaryl polyglycol ether
Water: 987.50 parts by weight The amount of active compound required for the desired active compound concentration in the spray liquor was mixed with the stated amount of the solvent and of the dispersing agent and the concentrate was diluted with the stated amount of water.

30 rice plants which were about 40 days old were sprayed with the spray liquor until dripping wet. The plants remained in a greenhouse, at temperatures of 22 to 24 deg. C. and a relative atmospheric humidity of about 70%, until they had dried. Needles were then dipped into an aqueous bacterial suspension of *Xanthomonas oryzae* and the plants were inoculated by pricking the leaves. After the inoculation, the leaves stood for 24 hours at 100% relative atmospheric humidity and thereafter in a room at 26 to 28 deg. C. and 80% relative atmospheric humidity.

10 days after the inoculation, the infection of all pricked inoculated leaves of plants which had beforehand been treated with the preparation was evaluated.

In this test, for example, the following compounds from the preparation examples showed a superior action compared with the prior art: (27), (4), (38), (14) and (29).

It will be appreciated that the instant specification and examples are set forth by way of illustration and not limitation, and that various modifications and changes may be made without departing from the spirit and scope of the present invention.

We claim:

1. An N-(4-substituted-phenyl)-N'-(2-substituted-benzoyl)-thiourea of the formula

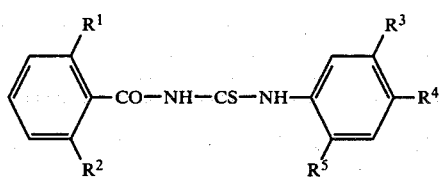

in which

R[1] represents halogen,

R[2] represents hydrogen or halogen,

R[3] represents hydrogen, halogen or halogenoalkyl,

R[4] represents halogen, halogenoalkyl, halogenoalkoxy, halogenoalkylthio or halogenoalkylsulphonyl, with the proviso that R[3] represents halogenoalkyl if R[4] represents halogen, and R[5] represents hydrogen or halogen.

2. A compound according to claim 1, in which

R[2] represents hydrogen, fluorine or chlorine,

R[3] represents hydrogen, chlorine or trifluoromethyl,

R[4] represents chlorine, fluoro- or chlorofluoroalkyl, fluoro- or chlorofluoro-alkoxy, fluoro- or chlorofluoro-alkylthio or fluoroalkylsulphonyl, the alkyl moiety in each case containing 1 or 2 carbon atoms, with the proviso that R[3] represents trifluoromethyl if R[4] represents chlorine, and R[5] represents hydrogen or chlorine.

3. A compound according to claim 1, wherein such compound is N-(2-chlorobenzoyl)-N'-(4-trifluoromethoxy-phenyl)-thiourea of the formula

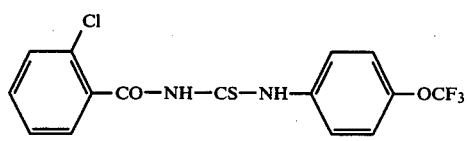

4. A compound according to claim 1, wherein such compound is N-(2-chlorobenzoyl)-N'-[3-chloro-4-(2-chloro-1,1,2-trifluoroethoxy)-phenyl]-thiourea of the formula

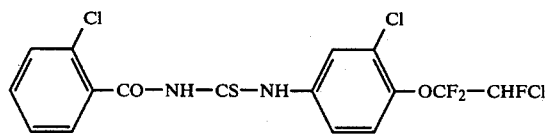

5. A compound according to claim 1, wherein such compound is N-(2-chloro-6-fluorobenzoyl)-N'-(4-trifluoromethoxy-phenyl)-thiourea of the formula

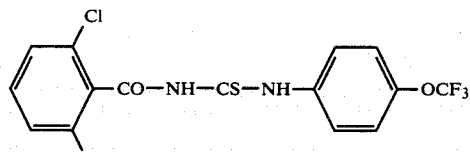

6. A compound according to claim 1, wherein such compound is N-(2-chloro-6-fluorobenzoyl)-N'-(4-trifluoromethylmercaptophenyl)-thiourea of the formula

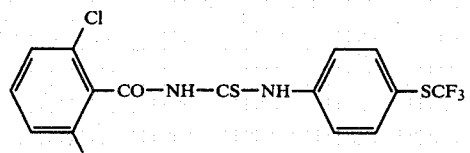

7. A compound according to claim 1, wherein such compound is N-(2,6-difluorobenzoyl)-N'-(4-trifluoromethoxy-phenyl)-thiourea of the formula

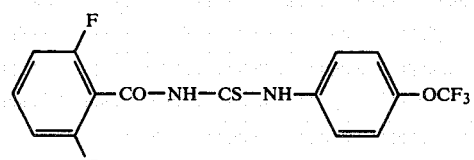

8. An arthropodicidal, fungicidal or bactericidal composition containing as active ingredient an arthropodicidally, fungicidally or bactericidally effective amount of a compound according to claim 1 in admixture with a diluent.

9. A method of combating arthropods or phytopathogenic fungi or bacteria, which comprises applying to the arthropods, fungi or bacteria, or a habitat thereof, an arthropodicidally, fungicidally or bactericidally effective amount of a compound according to claim 1.

10. The method according to claim 9, wherein such compound is N-(2-chlorobenzoyl)-N'-(4-trifluoromethoxy-phenyl)-thiourea, N-(2-chlorobenzoyl)-N'-[3-chloro-4-(2-chloro-1,1,2-trifluoroethoxy)-phenyl]-thiourea, N-(2-chloro-6-fluorobenzoyl)-N'-(4-trifluoromethylmercaptophenyl)-thiourea, N-(2,6-difluorobenzoyl)-N'-(4-trifluoromethoxy-phenyl)-thiorea, N-(2,6-difluorobenzoyl)-N'-trifluoromethylthio-phenyl)-thiourea.

11. A compound according to claim 1, wherein such compound is N-(2,6-difluorobenzoyl)-N'-(trifluoromethylthio-phenyl)-thiourea of the formula

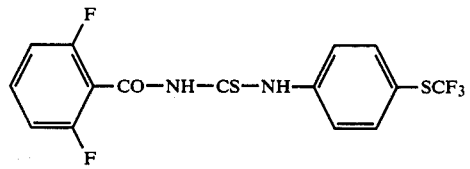

* * * * *